United States Patent
Kojima et al.

(10) Patent No.: US 9,662,135 B2
(45) Date of Patent: May 30, 2017

(54) FLUID EJECTION DEVICE AND MEDICAL APPARATUS

(71) Applicant: SEIKO EPSON CORPORATION, Tokyo (JP)

(72) Inventors: Hideki Kojima, Matsumoto (JP); Kazuaki Uchida, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 210 days.

(21) Appl. No.: 14/227,902

(22) Filed: Mar. 27, 2014

(65) Prior Publication Data
US 2014/0296896 A1   Oct. 2, 2014

(30) Foreign Application Priority Data
Mar. 29, 2013   (JP) .................................. 2013-071219

(51) Int. Cl.
*A61B 17/3203*   (2006.01)
(52) U.S. Cl.
CPC ..... *A61B 17/3203* (2013.01); *A61B 2017/32032* (2013.01); *A61B 2218/007* (2013.01); *A61B 2560/02* (2013.01)
(58) Field of Classification Search
CPC ...... A61B 17/3203; A61B 2017/32032; A61B 2017/32035; A61B 17/32037; F04B 43/046; F04B 45/047
See application file for complete search history.

(56) References Cited

U.S. PATENT DOCUMENTS

| | | | |
|---|---|---|---|
| 5,674,226 A | * | 10/1997 | Doherty ............. A61B 17/3203 604/44 |
| 7,901,374 B2 | | 3/2011 | Seto et al. |
| 2009/0043480 A1 | | 2/2009 | Seto et al. |
| 2009/0270799 A1 | | 10/2009 | Seto et al. |
| 2010/0069937 A1 | | 3/2010 | Seto et al. |

(Continued)

FOREIGN PATENT DOCUMENTS

| | | |
|---|---|---|
| GB | 2 176 110 A | 12/1986 |
| JP | S61-279239 A | 12/1986 |

(Continued)

OTHER PUBLICATIONS

Extended European Search Report dated Jul. 8, 2014 as received in Application No. 14161975.9.

*Primary Examiner* — Thomas McEvoy
(74) *Attorney, Agent, or Firm* — Maschoff Brennan

(57) ABSTRACT

A fluid ejection device includes a fluid chamber, a volume varying unit, a fluid supplying unit, and an ejection pipe. The volume varying unit generates pulsation in the pressure of a fluid in the fluid chamber. The fluid supplying unit supplies the fluid to the fluid chamber through a first channel. The ejection pipe receives the supply of the fluid, in which the pulsation is generated, from the fluid chamber through a second channel and ejects the supplied fluid from an ejection port. In a connecting part to the fluid chamber, the cross-sectional area of the second channel is five times or more as large as the cross-sectional area of the first channel. In the connecting part to the fluid chamber, the first channel and the second channel are arranged to be opposed to each other via the vicinity of the center of the fluid chamber.

11 Claims, 3 Drawing Sheets

(56) References Cited

U.S. PATENT DOCUMENTS

| | | |
|---|---|---|
| 2010/0082053 A1 | 4/2010 | Hama et al. |
| 2011/0208224 A1 | 8/2011 | Kojima |
| 2012/0181352 A1 | 7/2012 | Seto et al. |
| 2014/0371773 A1 | 12/2014 | Kojima et al. |

FOREIGN PATENT DOCUMENTS

| | | |
|---|---|---|
| JP | 2007-151783 A | 6/2007 |
| JP | 2008-082202 A | 4/2008 |
| JP | 2009-056320 A | 3/2009 |
| JP | 2010-057531 A | 3/2010 |
| JP | 2010-059792 A | 3/2010 |
| JP | 2010-059902 A | 3/2010 |
| JP | 2010-084565 A | 4/2010 |
| JP | 2010-053767 A | 11/2010 |
| JP | 2012-082739 A | 4/2012 |
| JP | 2012-145031 A | 8/2012 |

* cited by examiner

FLUID EJECTION DEVICE AND MEDICAL APPARATUS

This application claims the benefit of Japanese Patent Application No. 2013-71219, filed on Mar. 29, 2013. The content of the aforementioned application is incorporated herein by reference in its entirety.

BACKGROUND

1. Technical Field

The present invention relates to ejection of fluid.

2. Related Art

There is known a fluid ejection device that varies the volume of a fluid chamber using an actuator including a piezoelectric element and generates pulsation in the pressure of the fluid in the fluid chamber to thereby intermittently eject the fluid (e.g., JP-A-2008-82202).

A problem of the related art is that air bubbles tend to accumulate in the fluid chamber. The air bubbles in the fluid chamber are generated from the fluid in the fluid chamber by the volume variation of the fluid chamber. When the air bubbles accumulate in the fluid chamber, the volume variation of the fluid chamber is absorbed by volume variation of the air bubbles. Therefore, appropriate pulsation sometimes cannot be generated.

SUMMARY

An advantage of some aspects of the invention is to solve at least a part of the problems described above, and the invention can be implemented as the following aspects.

(1) An aspect of the invention provides a fluid ejection device. The fluid ejection device includes: a pulsation giving unit for ejecting fluid in a fluid chamber; a fluid supplying unit configured to supply the fluid to the fluid chamber through a first channel; and an ejection pipe configured to communicate with a second channel, which communicates with the pulsation giving unit, and eject the fluid from an ejection port. The cross-sectional area of the second channel is five times or more as large as the cross-sectional area of the first channel. A connecting part of the first channel and the fluid chamber and a connecting part of the second channel and the fluid chamber are arranged in positions opposed to each other via the vicinity of the center of the fluid chamber. According to this aspect of the invention, air bubbles in the fluid chamber are easily discharged through the ejection pipe. This is because, since the connecting part of the first channel and the fluid chamber and the connecting part of the second channel and the fluid chamber are arranged in the positions opposed to each other via the vicinity of the center of the fluid chamber, a flow in the fluid chamber less easily stagnate and, in addition, since the cross-sectional area of the second channel is five times or more as large as the cross-sectional area of the first channel, the air bubbles easily flows into the ejection pipe.

(2) Another aspect of the invention provides the fluid ejection device according to the aspect described above, wherein the connecting part of the second channel and the fluid chamber is arranged in a position closer to an edge of the fluid chamber than the connecting part of the first channel and the fluid chamber. According to this aspect of the invention, the air bubbles in the fluid chamber are more easily discharged. This is because, since the connecting part of the second channel and the fluid chamber is arranged in the position closer to the edge of the fluid chamber than the connecting part of the first channel and the fluid chamber, the air bubbles are suppressed from accumulating between the second channel and the edge of the fluid chamber.

(3) Still another aspect of the invention provides the fluid ejection device according to the aspect described above, wherein the fluid ejection device further includes a guiding section configured to guide a user to use the fluid ejection device in a state in which the connecting part of the second channel and the fluid chamber is located above the connecting part of the first channel and the fluid chamber in the vertical direction. According to this aspect of the invention, the air bubbles in the fluid chamber are more easily discharged. Since the guiding section guide the user to use the fluid ejection device in the state in which the connecting part of the second channel and the fluid chamber is located above the connecting part of the first channel and the fluid chamber in the vertical direction, it is more likely that the fluid ejection device is used in the state in which the connecting part of the second channel and the fluid chamber is located above the connecting part of the first channel and the fluid chamber. If the fluid ejection device is used in the state in which the connecting part of the second channel and the fluid chamber is located above the connecting part of the first channel and the fluid chamber, the air bubbles easily move to the vicinity of the connecting part of the second channel and the fluid chamber with buoyancy according to the influence of the gravity. As a result, it is possible to obtain the effect explained above.

(4) This aspect of the invention provides the fluid ejection device according to the aspect described above, wherein the fluid ejection device further includes: a suction channel for sucking the fluid present around the ejection port; a container configured to house at least apart of the ejection pipe, at least a part of fluid supplying channel connecting the fluid supplying unit and the first channel, the pulsation giving unit, and at least a part of the suction channel; and a suction adjusting mechanism for adjusting a degree of suction by the suction channel, the suction adjusting mechanism includes an operation unit provided in the container, and the guiding section is the operation unit. According to this aspect of the invention, it is possible to realize the guide using the operation unit.

(5) Yet another aspect of the invention provides the fluid ejection device according to the aspect described above, wherein the fluid ejection device further includes a container configured to house at least a part of the ejection pipe, at least a part of fluid supplying channel connecting the fluid supplying unit and the first channel, and the pulsation giving unit, and the guiding section is a grip provided in the container. According to this aspect of the invention, it is possible to realize the guide using the grip.

(6) Still yet another aspect of the invention provides the fluid ejection device according to the aspect described above, wherein the fluid ejection device further includes a container configured to house apart of the ejection pipe, at least a part of fluid supplying channel connecting the fluid supplying unit and the first channel, and the pulsation giving unit, and the guiding section is a curved section located on the outside of the container as a part of the ejection pipe. According to this aspect of the invention, it is possible to realize the guide using the curved section.

(7) Further another aspect of the invention provides a fluid ejection device including: a volume varying unit configured to generate pulsation in fluid in a fluid chamber; a fluid supplying unit configured to supply the fluid to the fluid chamber through a first channel; an ejection pipe configured to receive the supply of the fluid, in which the pulsation is generated, from the volume varying unit through a second channel and eject the supplied fluid from an ejection port; and an up down direction defining unit configured to define an up down direction of the volume varying unit. The cross-sectional area of the second channel is larger than the cross-sectional area of the first channel. The second channel is arranged above the first channel on the basis of the definition by the up down direction defining unit. According to this aspect of the invention, air bubbles in the fluid chamber are easily discharged through the ejection pipe. This is because the second channel is arranged above the first channel and, in addition, the cross-sectional area of the second channel is larger than the cross sectional area of the first channel.

(8) Still further another aspect of the invention provides a medical apparatus including the fluid ejection device according to the aspect of the invention described above. According to this aspect of the invention, it is possible to provide a medical apparatus including the fluid ejection device in which air bubbles less easily accumulate in the fluid chamber.

Not all of the plurality of components of the aspects of the invention explained above are essential. In order to solve a part or all of the problems explained above or in order to attain a part or all of the effects described in this specification, a part of the plurality of components can be changed, deleted, and replaced with other new components as appropriate and delete a part of limitations of the components. In order to solve a part or all of the problems explained above or in order to attain a part or all of the effects described in this specification, a part or all of the technical features included in one of the aspects of the invention explained above can be combined with a part or all of the technical features included in the other aspects of the invention as an independent form of the invention.

For example, one of the aspects of the invention can be implemented as a device including a part or all of the volume varying unit, the fluid supplying unit, and the ejection pipe. The device may include or may not include the volume varying unit. The device may or may not include the fluid supplying unit. The device may or may not include the ejection pipe. For example, the volume varying unit may vary the volume in the fluid chamber. For example, the fluid supplying unit may supply the fluid to the fluid chamber through the first channel. For example, the ejection pipe may communicate with the second channel, which communicates with the volume varying unit, and eject the fluid from the ejection port. The cross-sectional area of the second channel may be five times or more as large as the cross-sectional area of the first channel. The first channel and the second channel may be arranged to be opposed to each other via the vicinity of the center of the volume varying unit. Such a device can be implemented as, for example, a fluid ejection device and can be implemented as devices other than the fluid ejection device. According to such a form, it is possible to solve at least one of the various objects such as a reduction in the size of the device, a reduction in costs, resource saving, simplification of manufacturing, and improvement of convenience of use. A part or all of the technical features of the aspects of the fluid ejection device explained above can be applied to this device.

The invention can also be implemented in various forms other than the forms explained above. For example, the invention can be implemented in forms such as a fluid ejection method, a surgical operation method, computer programs for implementing these methods, and storage media having these computer programs stored therein.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
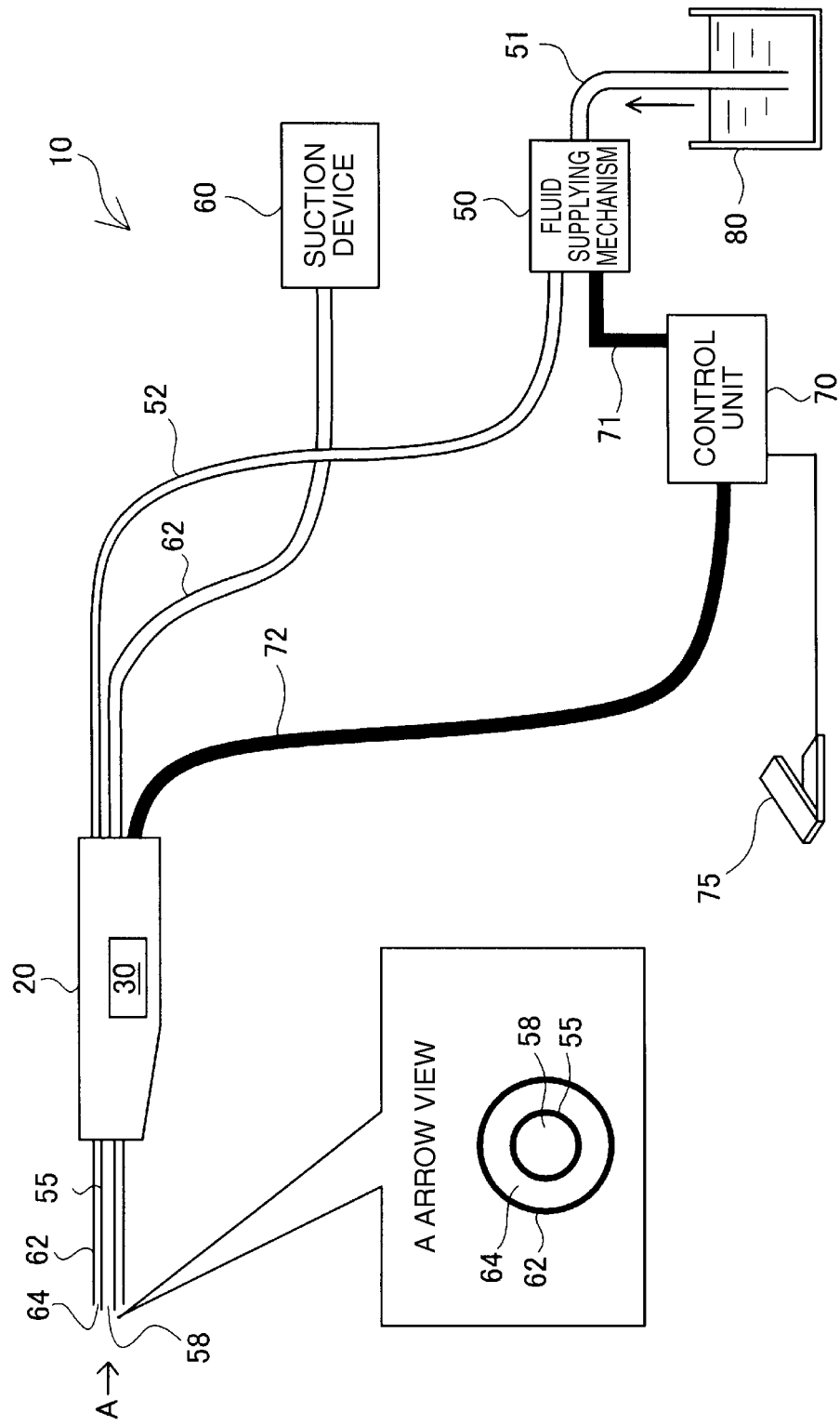
FIG. 1 is a configuration diagram of a fluid ejection device in a first embodiment.

FIG. 1 shows the configuration of a fluid ejection device 10. The fluid ejection device 10 is a medical device used in a medical institution. The fluid ejection device 10 has a function of incising or excising an affected part by ejecting fluid to the affected part.

The fluid ejection device 10 includes a hand piece 20, a fluid supplying mechanism 50, a suction device 60, a control unit 70, and a fluid container 80. The fluid supplying mechanism 50 and the fluid container 80 are connected to each other by a connection tube 51. The fluid supplying mechanism 50 and the hand piece 20 are connected to each other by a fluid supplying channel 52. At least a part of the connection tube 51 and the fluid supplying channel 52 are formed of resin. At least a part of the connection tube 51 and the fluid supplying channel 52 may be formed of a material (e.g., rubber or metal) other than the resin.

The fluid container 80 stores saline. The fluid supplying mechanism 50 supplies fluid sucked from the fluid container 80 via the connection tube 51 to the hand piece 20 via the fluid supplying channel 52.

The hand piece 20 is an instrument held and operated by a user of the fluid ejection device 10. A pulsation generating unit 30 incorporated in the hand piece 20 generates pulsation of the pressure of the fluid supplied to the hand piece 20 from the fluid supplying mechanism 50 via the fluid supplying channel 52. The fluid, in which the pulsation of the pressure is generated, is supplied to an ejection pipe 55. The fluid supplied to the ejection pipe 55 is intermittently ejected from an ejection port 58. The user hits the fluid ejected from the ejection port 58 on an affected part to thereby incise or excise the affected part. The ejection pipe 55 is formed of stainless steel. At least a part of the ejection pipe 55 may be formed of other materials having predetermined or higher rigidity such as other kinds of metal such as brass and reinforced plastics.

The control unit 70 transmits a drive signal to the pulsation generating unit 30 via a signal cable 72. The control unit 70 controls the fluid supplying mechanism 50 via a control cable 71 to thereby control a flow rate of the fluid supplied to the pulsation generating unit 30. A foot switch 75 is connected to the control unit 70. When the user turns on the foot switch 75, the control unit 70 controls the fluid supplying mechanism 50 to execute the supply of the fluid to the pulsation generating unit 30. The control unit 70 transmits the drive signal to the pulsation generating unit 30 and causes the pulsation generating unit 30 to generate pulsation in the pressure of the fluid supplied to the pulsation generating unit 30.

The suction device 60 is a device for sucking the fluid and an excised object around the ejection port 58. The suction device 60 and the hand piece 20 are connected to each other by a suction channel 62. The suction channel 62 pierces through the hand piece 20 and opens near the distal end of the ejection pipe 55. The suction channel 62 covers the ejection pipe 55 in the hand piece 20 to thereby form a cylinder in which the wall of the ejection pipe 55 and the wall of the suction channel 62 are substantially concentric as shown in an A arrow view of FIG. 1. A channel through which a sucked object sucked from a suction port 64, which is the distal end of the suction channel 62, flows is formed between the outer wall of the ejection pipe 55 and the inner wall of the suction channel 62. The sucked object is sucked by the suction device 60 via the suction channel 62.

Figure 2:
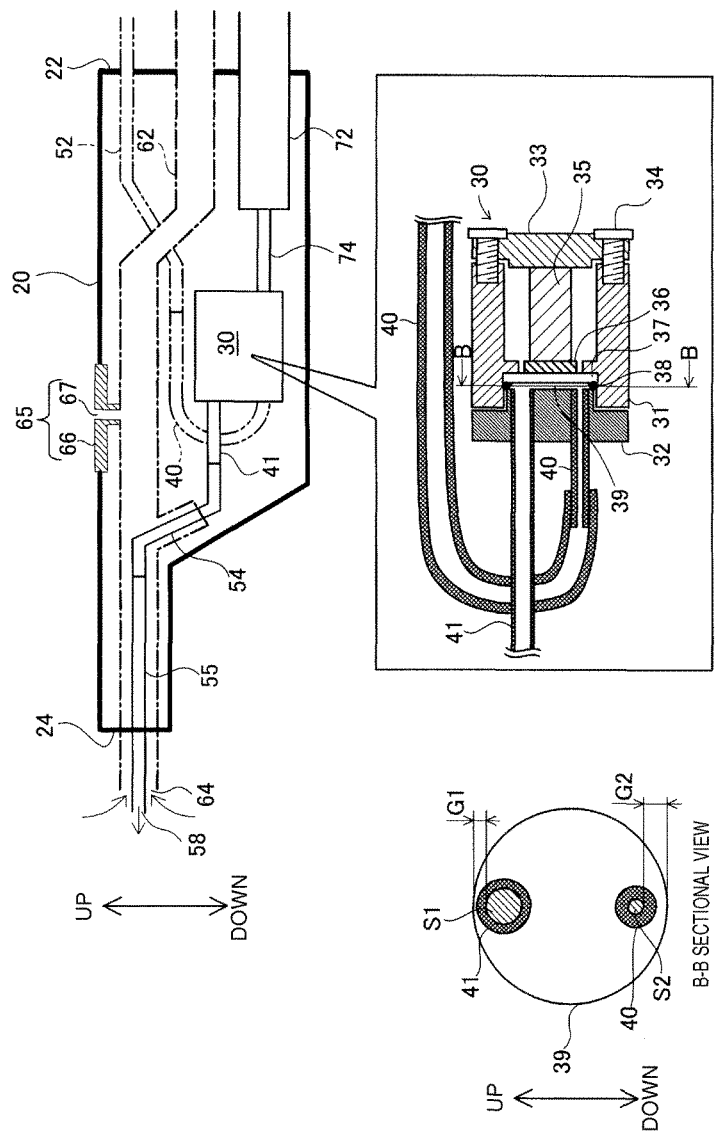
FIG. 2 is an internal structure diagram of a hand piece.

FIG. 2 shows the internal structure of the hand piece 20. The hand piece 20 incorporates a pulsation generating unit 30, an inlet channel 40, an outlet channel 41, and a connection tube 54 and includes a suction force adjusting mechanism 65.

The pulsation generating unit 30 includes, as shown in the lower part of FIG. 2, a first case 31, a second case 32, a third case 33, bolts 34, a piezoelectric element 35, a reinforcing plate 36, a diaphragm 37, a gasket 38, the inlet channel 40, and the outlet channel 41. The first case 31 and the second case 32 are opposed and joined to each other. The first case 31 is a cylindrical member. One end portion of the first case 31 is closed by fixing the third case 33 with the bolts 34. The piezoelectric element 35 is arranged in a space formed on the inside of the first case 31.

The piezoelectric element 35 is a laminated piezoelectric element. One end of the piezoelectric element 35 is fixedly attached to the diaphragm 37 via the reinforcing plate 36. The other end of the piezoelectric element 35 is fixedly attached to the third case 33. The diaphragm 37 is made of a metal thin film. The peripheral edge portion of the diaphragm 37 is fixedly attached to the first case 31. A fluid chamber 39 is formed between the diaphragm 37 and the second case 32. The volume of the fluid chamber 39 is varied by the driving of the piezoelectric element 35.

The signal cable 72 is inserted from a rear end portion 22 of the hand piece 20. Two electrode lines 74 are housed in the signal cable 72 and connected to the piezoelectric element 35 in the pulsation generating unit 30. The drive signal transmitted from the control unit 70 is transmitted to the piezoelectric element 35 via the electrode lines 74 in the signal cable 72. The piezoelectric element 35 expands and contracts on the basis of the drive signal.

The inlet channel 40, into which the fluid flows, is connected to the second case 32. The inlet channel 40 is bent in a U shape and extends toward the rear end portion 22 of the hand piece 20. The fluid supplying channel 52 is connected to the inlet channel 40. The fluid supplied from the fluid supplying mechanism 50 is supplied to the fluid chamber 39 via the fluid supplying channel 52.

The piezoelectric element 35 expands and contracts at a predetermined frequency (e.g., 10 to 1000 Hz), the diaphragm 37 vibrates. When the diaphragm 37 vibrates, the volume of the fluid chamber 39 varies and the pressure of the fluid in the fluid chamber 39 pulsates. The fluid passed through the fluid chamber 39 flows out from the outlet channel 41.

The outlet channel 41 is connected to the second case 32. The ejection pipe 55 is connected to the outlet channel 41 via the connection tube 54. The fluid flowed out to the outlet channel 41 is ejected from the ejection port 58 through the connection tube 54 and the ejection pipe 55.

On the other hand, the suction force adjusting mechanism 65 is a mechanism for adjusting a force of the suction channel 62 for sucking the fluid or the like from the suction port 64. The suction force adjusting mechanism 65 includes an operation unit 66 and a hole 67. The hole 67 is a through-hole that connects the suction channel 62 and the operation unit 66. When the user opens and closes the hole 67 with a finger of the hand that grips the hand piece 20, an amount of the air flowing into the suction channel 62 via the hole 67 is adjusted according to a degree of the opening and closing. Consequently, a suction force of the suction port 64 is adjusted. The adjustment of the suction force can also be realized by control by the suction device 60.

The hole 67 is preferably faced upward in the vertical direction because a sucked object is discharged to the outside from the hole 67 by gravity. This phenomenon guides the user to grip the hand piece 20 in a posture in which the hole 67 is faced upward in the vertical direction. In the following explanation, the axial direction of the hole 67 is defined as "up down direction". A direction from a connecting place of the hole 67 and the suction channel 62 to an opening section of the hole 67 is defined as "upward in the up down direction". In the following explanation, when "upward" is simply referred to, this indicates upward in the up down direction.

In the fluid ejection device 10, when the hole 67 is faced upward, the positions of the components are determined to make the function and operability of the suction force adjusting mechanism 65 preferable. However, the suction force adjusting mechanism 65 does not force the user to adopt a certain method of use of the hand piece 20.

As shown in the B-B sectional view of FIG. 2, a connecting part of the fluid chamber 39 and the outlet channel 41 (hereinafter referred to as "outlet part") and a connecting part of the fluid chamber 39 and the inlet channel 40 (hereinafter referred to as "inlet part") are arranged to be opposed to each other via the vicinity of the center of the fluid chamber 39. The outlet part is arranged above the inlet part. Therefore, air bubbles easily move to the vicinity of the outlet part with buoyancy according to the influence of the gravity. Discharge of the air bubbles is facilitated. A relation of upper and lower is not limited to a positional relation of right above and right under and also include a relation of high and low. A channel area S1 of the outlet part is larger than a channel area S2 of the inlet part and is, for example, five times as large as the channel area S2. According to the arrangement and the difference of the channel areas, when the volume of the fluid chamber 39 varies, a backflow of the fluid to the inlet channel 40 is suppressed and the discharge of the air bubbles from the fluid chamber 39 to the inlet channel 40 is facilitated. Consequently, the discharge of the remaining air bubbles discharged during filling of the fluid and mixed air bubbles during use is facilitated. The pressure of the fluid in the fluid chamber 39 properly pulsates. The vicinity of the center of the fluid chamber 39 is the center of the side surface of the fluid chamber 39 to which the inlet part and the outlet part are connected. When the distance from the center to the side surface is represented as t, the vicinity of the center of the fluid chamber 39 is within a range of 0.25t.

As shown in the B-B sectional view of FIG. 2, a distance G1 from the inner wall of the outlet part to the edge of the fluid chamber 39 is shorter than a distance G2 from the inner wall of the inlet part to the edge of the fluid chamber 39. Consequently, the air bubbles less easily accumulate between the inner wall of the outlet channel 41 and the edge of the fluid chamber 39.

A correspondence relation between the first embodiment and the appended claims is explained. The hand piece 20 corresponds to a container, the piezoelectric element 35 and the diaphragm 37 correspond to a volume varying unit, the inlet channel 40 corresponds to a first channel, the outlet channel 41 corresponds to a second channel, the fluid supplying mechanism 50 corresponds to a fluid supplying unit, and the suction force adjusting mechanism 65 corresponds to a guiding section and an up down direction defining unit.

Figure 3:
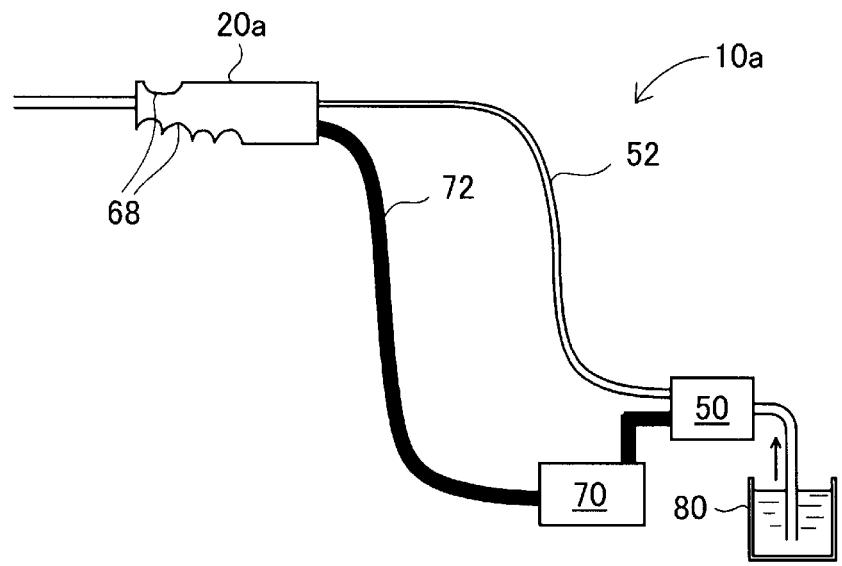
FIG. 3 is a configuration diagram of a fluid ejection device in a second embodiment.

FIG. 3 shows the configuration of a fluid ejection device 10*a* in a second embodiment. The fluid ejection device 10*a* is different from the fluid ejection device 10 in the first embodiment in that the fluid ejection device 10*a* includes a hand piece 20*a* instead of the hand piece 20.

The hand piece 20*a* includes a grip 68 including concave and convex shapes on the outer side as shown in FIG. 3. The grip 68 makes it easy to grip the hand piece 20*a* and guides a user to grip the hand piece 20*a* in a posture in which the outlet channel 41 is located above the inlet channel 40. That is, the grip 68 corresponds to the guiding section in the appended claims.

Figure 4:
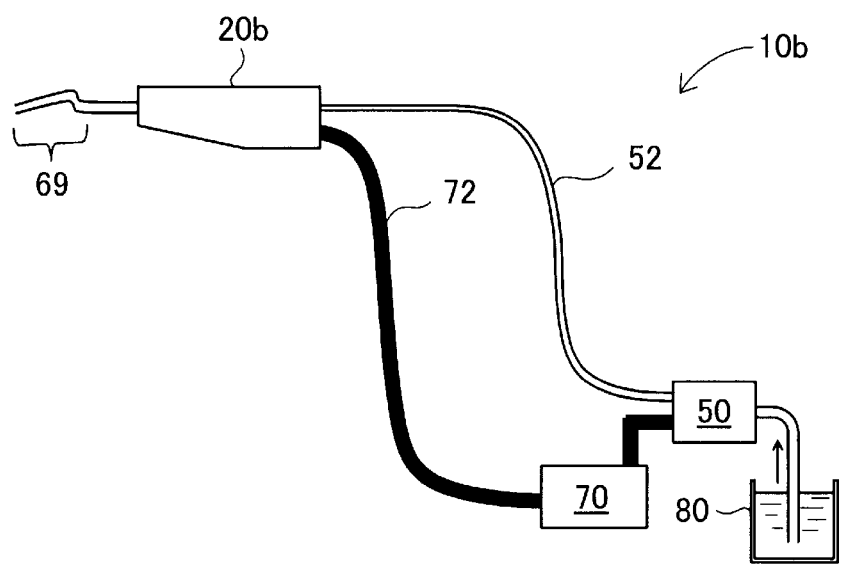
FIG. 4 is a configuration diagram of a fluid ejection device in a third embodiment.

FIG. 4 shows the configuration of a fluid ejection device 10*b* in a third embodiment. The fluid ejection device 10*b* is different from the fluid ejection device 10 in the first embodiment in that the fluid ejection device 10*b* includes a hand piece 20*b* instead of the hand piece 20.

The hand piece 20*b* includes a curved section 69 as shown in FIG. 4. The curved section 69 is a part of the ejection pipe 55 and is a part curved in a part exposed from the hand piece 20*b*. The curved section 69 bends in a direction parallel to a specific plane and does not bend in a direction orthogonal to the specific plane. The specific plane is a plane including the up down direction and the axis of the ejection pipe 55 in a straight part.

The curved section 69 makes it easy to eject the fluid to a target position and guides a user to grip the hand piece 20*b* in a posture in which the outlet channel 41 is located above the inlet channel 40. That is, the curved section 69 corresponds to the guiding section in the appended claims.

The invention is not limited to the embodiments, examples, and modifications described in this specification and can be realized in various configurations without departing from the spirit of the invention. For example, technical features of the embodiments, the examples, and the modifications corresponding to technical features in the forms described in the summary of the invention can be replaced or combined as appropriate in order to solve a part or all of the problems explained above or attain a part or all of the effects explained above. Unless the technical features are not explained in this specification as essential technical features, the technical features can be deleted as appropriate. Technical features explained below are examples of such technical features.

A method of realizing the guiding section may be a combination of a plurality of methods. For example, two or three among the suction force adjusting mechanism, the grip, and the curved section may be combined or other methods may be further combined. The area of the outlet channel may be smaller or larger than five times with respect to the area of the inlet channel.

The up down direction may be defined by drawing, on the hand piece, a line work such as an arrow or a character indicating the up down direction. The up down direction of the hand piece may be defined by forming the sectional shape of the hand piece as an ellipse and drawing out the ejection pipe from above the center of the ellipse at the distal end portion of the hand piece. An inclination sensor and a level may be mounted on the hand piece to inform the user of the up down direction using results of measurement by the inclination sensor and the level. A posture of the hand piece may be read using a sensor provided on the outside of the hand piece to inform the user of the up down direction.

The up down direction defining unit may be realized by a function exerted by the hand piece alone. The up down direction defining unit may be realized by a function exerted by a device other than the hand piece and included in the fluid ejection device. The up down direction defining unit may be realized by a function exerted by the fluid ejection device and another device in cooperation with each other.

The up down direction defining unit may define the up down direction as a direction of use of the container when the user uses the fluid ejection device. When the function and the characteristic of the fluid ejection device change according to the direction of the container, the up down direction defining unit may define the up down direction of the container on the basis of a direction of the container in which the function and the characteristics are suitably exerted. The up down direction defining unit may provide the user of the fluid ejection device with information for defining the up down direction of the container with respect to at least any one of the visual sense, the tactile sense, the auditory sense, and the like of the user. The up down direction defining unit may guide the user to use the container in a predetermined posture using various elements included in the fluid ejection device. The various elements are a shape, a pattern, a color, a line work, a character, a mark, sound, light, operability, design, and the like. The up down direction defining unit may suppress, with the various elements included in the fluid ejection device, the user from using the fluid ejection device in a direction other than the up down direction defined in advance.

The fluid ejection device may be used in apparatuses other than the medical apparatus. For example, the fluid ejection device may be used in a cleaning apparatus that removes stains using ejected fluid. The fluid ejection device may be used in a rendering apparatus that draws a line or the like using ejected fluid.

What is claimed is:

1. A fluid ejection device comprising:
   a pulsation giving unit for ejecting fluid in a fluid chamber;
   a fluid supplying unit configured to supply the fluid to the fluid chamber through a first channel; and
   an ejection pipe configured to communicate with a second channel, which communicates with the pulsation giving unit, and eject the fluid from an ejection port, wherein
   a cross-sectional area of the second channel is five times or more as large as a cross-sectional area of the first channel,
   a connecting part of the first channel and the fluid chamber and a connecting part of the second channel to the fluid chamber are arranged in positions opposed to each other with respect to a center of the fluid chamber;
   a guiding section configured to guide a user to use the fluid ejection device in a state in which the connecting part of the second channel and the fluid chamber is located above the connecting part of the first channel and the fluid chamber in the vertical direction;
   a suction channel for sucking the fluid present around the ejection port;
   a container configured to house at least a part of the ejection pipe, at least a part of fluid supplying channel connecting the fluid supplying unit and the first channel, the pulsation giving unit, and at least a part of the suction channel; and a suction adjusting mechanism for adjusting a degree of suction within in the suction channel, wherein:

the suction adjusting mechanism includes an operation unit provided in the container and the guiding section is the operation unit, the connecting part of the second channel is arranged at a position closer to an edge of the fluid chamber than the connecting part of the first channel, the ejection pipe changes direction, the suction adjustment mechanism has a hole section communicating with the outside of the container and the suction channel, a point at which the ejection pipe changes direction is located closer to the ejection port than to the pulsation giving unit, and the point at which the ejection pipe changes direction, the hole section, and the pulsation giving unit are arranged in that order.

2. The fluid ejection device according to claim 1, further comprising a container configured to house at least a part of the ejection pipe, at least a part of the fluid supplying unit, and the pulsation giving unit, wherein the guiding section is a grip provided in the container.

3. A medical apparatus comprising the fluid ejection device according to claim 2.

4. The fluid ejection device according to claim 1, further comprising a container configured to house a part of the ejection pipe, at least a part of the fluid supplying unit, and the pulsation giving unit, wherein the guiding section is a curved section located on a part of the ejection pipe not housed in the container.

5. A medical apparatus comprising the fluid ejection device according to claim 4.

6. A medical apparatus comprising the fluid ejection device according to claim 1.

7. The fluid ejection device according to claim 1, wherein a section of the ejection pipe which is disposed inside the suction channel is provided at a position closer to the ejection port than the suction adjustment mechanism of the container.

8. The fluid ejection device according to claim 1, wherein: the suction channel has a first section having a first cross-sectional area and a second section having a second cross-sectional area that is larger than the first cross-sectional area, the hole section being provided in the second section of the suction channel.

9. The fluid ejection device according to claim 1, wherein the first channel comprises a curved portion which curves upward from the connecting portion towards a back of a hand piece which houses the pulsation giving unit and from which the ejection pipe extends.

10. A fluid ejection device comprising:

a volume varying unit configured to generate pulsation in fluid in a fluid chamber;

a fluid supplying unit configured to supply the fluid to the fluid chamber through a first channel;

an ejection pipe configured to receive the supply of the fluid, in which the pulsation is generated, from the volume varying unit through a second channel and eject the supplied fluid from an ejection port;

an up down direction defining unit configured to define an up down direction of the volume varying unit;

a cross-sectional area of the second channel is five times or more as large as a cross-sectional area of the first channel;

a connecting part of the first channel and the fluid chamber and a connecting part of the second channel to the fluid chamber are arranged in positions opposed to each other with respect to a center of the fluid chamber;

a guiding section configured to guide a user to use the fluid ejection device in a state in which the connecting part of the second channel and the fluid chamber is located above the connecting part of the first channel and the fluid chamber in the vertical direction;

a suction channel for sucking the fluid present around the ejection port;

a container configured to house at least a part of the ejection pipe, at least a part of fluid supplying channel connecting the fluid supplying unit and the first channel, the pulsation giving unit, and at least a part of the suction channel; and a suction adjusting mechanism for adjusting a degree of suction within in the suction channel, wherein:

the suction adjusting mechanism includes an operation unit provided in the container and the guiding section is the operation unit, the connecting part of the second channel is arranged at a position closer to an edge of the fluid chamber than the connecting part of the first channel, the ejection pipe changes direction, the suction adjustment mechanism has a hole section communicating with the outside of the container and the suction channel, a point at which the ejection pipe changes direction is located closer to the ejection port than to the pulsation giving unit, the point at which the ejection pipe changes direction, the hole section, and the pulsation giving unit are arranged in that order, a cross-sectional area of the second channel is larger than a cross-sectional area of the first channel, and the second channel is arranged above the first channel as defined by the up down direction defining unit.

11. A medical apparatus comprising the fluid ejection device according to claim 10.

* * * * *